United States Patent
Albalat

(10) Patent No.: US 10,279,132 B2
(45) Date of Patent: May 7, 2019

(54) AGITATION APPARATUS

(71) Applicant: BIOSURGICAL S.L., Madrid (ES)

(72) Inventor: Alberto Martinez Albalat, Madrid (ES)

(73) Assignee: BIOSURGICAL S.L., Ajalvir (ES)

( * ) Notice: Subject to any disclaimer, the term of this patent is extended or adjusted under 35 U.S.C. 154(b) by 45 days.

(21) Appl. No.: 14/435,202

(22) PCT Filed: Nov. 7, 2013

(86) PCT No.: PCT/EP2013/073292
§ 371 (c)(1),
(2) Date: Apr. 13, 2015

(87) PCT Pub. No.: WO2014/072423
PCT Pub. Date: May 15, 2014

(65) Prior Publication Data
US 2015/0250957 A1   Sep. 10, 2015

(30) Foreign Application Priority Data

Nov. 12, 2012 (GB) .................................. 1220306.3

(51) Int. Cl.
*A61M 13/00* (2006.01)
*A61M 1/28* (2006.01)
(Continued)

(52) U.S. Cl.
CPC ............ *A61M 13/003* (2013.01); *A61M 1/28* (2013.01); *A61M 1/3627* (2013.01);
(Continued)

(58) Field of Classification Search
CPC .. A61M 13/006; A61M 13/003; A61M 13/00; A61M 5/44; A61M 2210/1017;
(Continued)

(56) References Cited

U.S. PATENT DOCUMENTS 3,592,191 A   7/1971   Jackson
4,735,603 A   4/1988   Goodson et al.
(Continued)

FOREIGN PATENT DOCUMENTS

BE   365554 A   11/1929
DE   3121868 A1   3/1982
(Continued)

OTHER PUBLICATIONS

PCT International Search Report, dated Jan. 13, 2014 in corresponding PCT Application No. PCT/EP2013/073292.
(Continued)

*Primary Examiner* — Jenna Zhang
(74) *Attorney, Agent, or Firm* — Ostrager Chong Flaherty & Broitman PC

(57) ABSTRACT

An apparatus (1) for providing agitation inside a patient's body cavity (C) is such that substantially all the fluid and/or content present in the body cavity (C) is agitated and comprises a gas source (6, 7); means for delivering gas (2) from the gas source (6, 7) into a patient's body cavity (C); and means for recovering gas (9) from the patient's body cavity (C). A gas-fluid separation device (9) and a securing device for use with the apparatus (1), a method for providing agitation inside a patient's body cavity (C), a method for administering a therapeutic fluid into a patient's cavity (C), a method for securing the agitation apparatus (1) to a patient using the securing device and a method for the separation of a gas from a fluid using the gas-fluid separation device (9) are also disclosed.

39 Claims, 11 Drawing Sheets

(51) Int. Cl.
*A61M 1/36* (2006.01)
*A61M 16/10* (2006.01)
*A61M 16/16* (2006.01)

(52) U.S. Cl.
CPC ....... *A61M 13/006* (2014.02); *A61M 16/1075* (2013.01); *A61M 16/16* (2013.01); *A61M 2202/0225* (2013.01); *A61M 2202/0468* (2013.01); *A61M 2205/3331* (2013.01); *A61M 2205/3368* (2013.01); *A61M 2205/3389* (2013.01); *A61M 2205/36* (2013.01); *A61M 2205/3606* (2013.01); *A61M 2205/502* (2013.01); *A61M 2205/75* (2013.01); *A61M 2209/088* (2013.01); *A61M 2230/50* (2013.01)

(58) Field of Classification Search
CPC .... A61M 2210/1021; A61M 2005/006; A61M 2202/0225
See application file for complete search history.

(56) References Cited

U.S. PATENT DOCUMENTS

| | | | | |
|---|---|---|---|---|
| 5,388,571 | A * | 2/1995 | Roberts | A61M 16/16 128/200.18 |
| 5,704,504 | A | 1/1998 | Bueno | |
| 5,722,393 | A | 3/1998 | Bartel et al. | |
| 5,814,012 | A * | 9/1998 | Fleenor | A61M 13/003 600/560 |
| 6,153,435 | A * | 11/2000 | Crystal | C12N 15/86 435/243 |
| 6,409,699 | B1 * | 6/2002 | Ash | A61M 1/1696 604/29 |
| 6,544,210 | B1 | 4/2003 | Trudel et al. | |
| 6,645,197 | B2 * | 11/2003 | Garrison | A61B 17/00234 600/560 |
| 2001/0039441 | A1 * | 11/2001 | Ash | A61M 1/3621 607/106 |
| 2004/0019313 | A1 | 6/2004 | Childers et al. | |
| 2005/0028551 | A1 * | 2/2005 | Noda | F04C 29/0064 62/434 |
| 2005/0137529 | A1 * | 6/2005 | Mantell | A61M 13/003 604/129 |
| 2007/0088275 | A1 * | 4/2007 | Stearns | A61M 1/28 604/164.01 |
| 2007/0106247 | A1 * | 5/2007 | Burnett | A61F 7/12 604/508 |
| 2009/0084718 | A1 | 4/2009 | Prisco et al. | |
| 2009/0084719 | A1 | 4/2009 | Childers et al. | |
| 2009/0084721 | A1 | 4/2009 | Yardinci et al. | |
| 2010/0185139 | A1 * | 7/2010 | Stearns | A61B 17/3474 604/26 |
| 2010/0286544 | A1 | 11/2010 | Tanaka et al. | |
| 2010/0298771 | A1 * | 11/2010 | Tan | A61M 5/44 604/113 |
| 2011/0164002 | A1 | 7/2011 | Hill et al. | |
| 2011/0208278 | A1 * | 8/2011 | Machold | A61F 7/12 607/106 |
| 2011/0277758 | A1 | 11/2011 | Dixon et al. | |
| 2012/0150101 | A1 * | 6/2012 | Stearns | A61B 17/3421 604/24 |

FOREIGN PATENT DOCUMENTS

| | | |
|---|---|---|
| JP | H0382461 A | 4/1991 |
| JP | 2000202022 A | 7/2000 |
| JP | 2000-296146 | 10/2000 |
| JP | 2000296146 A * | 10/2000 |
| WO | 9318704 A1 | 9/1993 |
| WO | 0016840 A1 | 3/2000 |
| WO | 2012084268 A1 | 12/2011 |

OTHER PUBLICATIONS

Search Report under Section 17(5) of the United Kingdom Patent Act 1977 from the Intellectual Property Office in priority UK Application No. GB1220306.3, dated May 28, 2014.
Combined Search & Examination Report under Sections 17 & 18(3) of the United Kingdom Patent Act 1977 from the Intellectual Property Office, Application No. GB1716595.2, dated Nov. 28, 2017.
Search results under Rule 164(2)(b) EPC in European Patent Application EP 13789277, dated May 11, 2018.
Notice of Grant from the Intellectual Property Office in UK, dated Jan. 2, 2018 in Application No. GB 1220306.3.
Notice of Grant from the Intellectual Property Office in UK, dated Oct. 23, 2018 in Application No. GB 1716595.2.

* cited by examiner

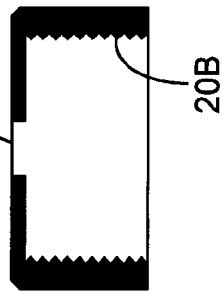
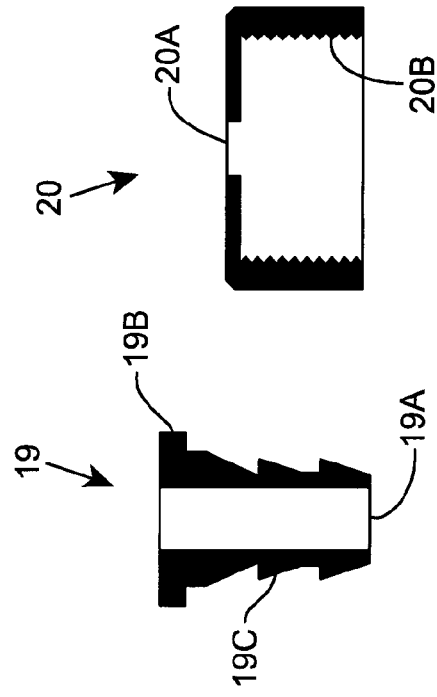
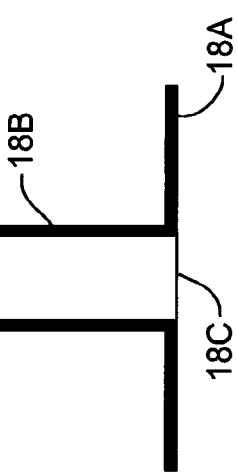
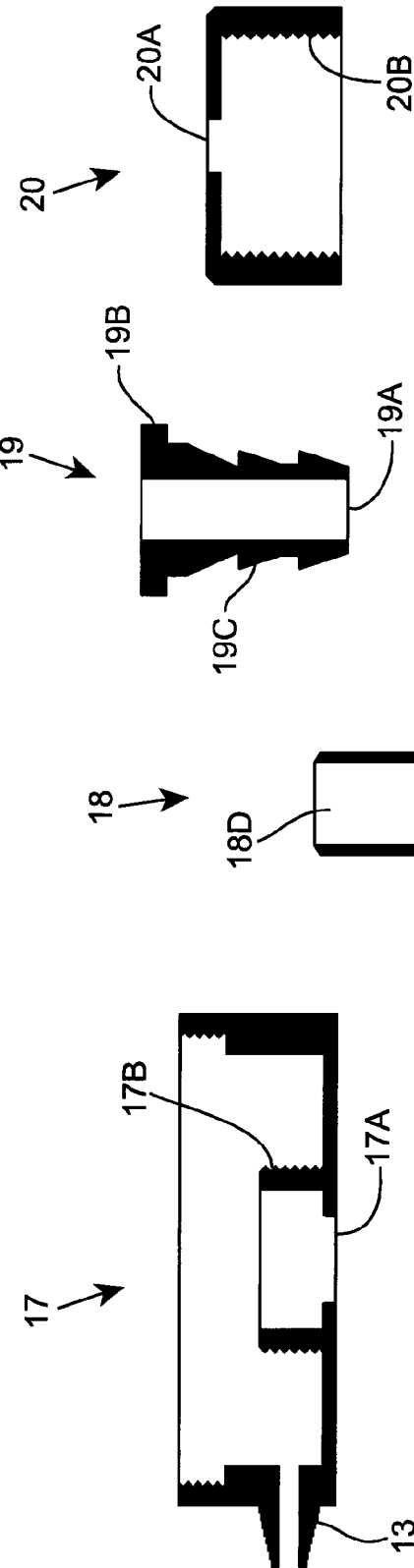
FIGURE 7A
FIGURE 7B
FIGURE 7C
FIGURE 7D

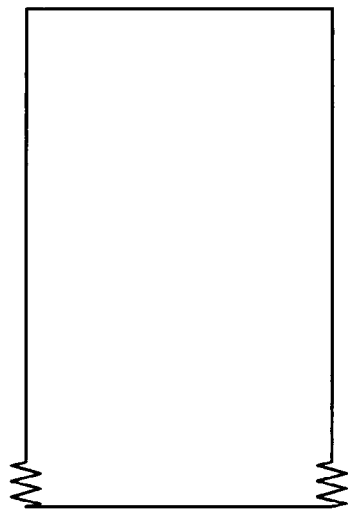
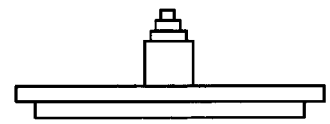
FIGURE 11B
FIGURE 11A
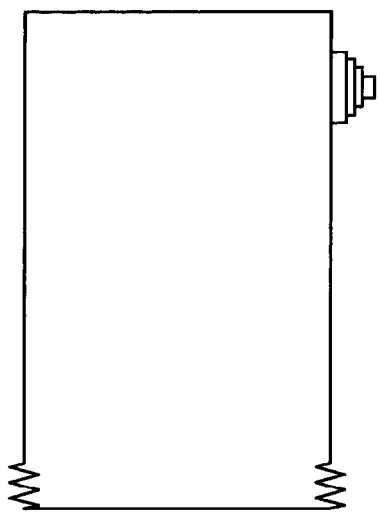
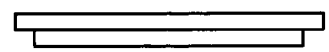
FIGURE 12B
FIGURE 12A

AGITATION APPARATUS

The present invention relates to a fluid agitation apparatus and method for the delivery, circulation and/or re-circulation of fluids, in particular heated or cooled therapeutic fluids.

Chemotherapy can involve the use of various types of drugs, for instance cytotoxic drugs to destroy cancerous cells. Conventionally, cytotoxic drugs are injected directly into a patient's bloodstream or are administered orally, in the form of tablets or capsules that breakdown such that the cytotoxic drugs enter the patient's bloodstream indirectly. Such techniques rely on the cytotoxic drugs circulating within the patient's bloodstream to reach the cancerous cells. Chemotherapy can be used on its own but also can also be used in conjunction with other types of treatments, such as cytoreductive surgery, radiotherapy and others, as a regular approach to combined cancer therapies.

The heat treatment, commonly known as hyperthermia, used in combination with any of the previously mentioned treatments, and in particular in combination with certain chemotherapy drugs, has shown promising results in several clinical studies. Hyperthermia has been shown to have a therapeutic effect on killing tumoral cells, since normally tumoral cells are more sensitive and less resistant to temperature increase when compared to normal healthy cells, but also to alter distribution of several drugs (increased absorption). In particular, hyperthermia has been shown to increase the effectiveness of standard chemotherapy treatments when used in combination.

Various surgical techniques have been developed to apply chemo-hyperthermia to treat different pathologies.

One of the most common type of hyperthermia treatment is the peritoneal chemo-hyperthermia. In this procedure, cytotoxic drugs are delivered to a patient's abdomen in the form of fluids via one or more catheters. The catheters can be inserted via a hole cut in the wall of a patient's abdomen or by laparoscopic techniques. The fluids may be introduced into a patient's abdomen through the catheter(s) and allowed to circulate within the abdomen and then withdrawn from the abdomen using a second (set of) catheter(s).

Different techniques have been described to execute this kind of procedure.

Some of the techniques, known as "open" techniques, involve opening a surgical access to the peritoneal cavity, exposing its content and fixing the borders of the access using a technique known as a "coliseum" technique. Since the patient's cavity is opened, there is a risk of contamination of the patient from contaminants in the treatment area, but equally, there is a risk of contamination of the treatment area by any chemotherapeutic fluid evaporating from the open cavity.

The peritoneal cavity is filled with the chemotherapeutic drug which can be heated using a recirculation system incorporating an external heat source. The temperature of the chemotherapeutic drug is critical in this type of treatment and a 10% loss is efficiency has been observed for each degree below 42° C. Thus, if a therapeutic fluid is circulated within a patient's body at too low a temperature the therapeutic fluid may not be as effective or, in extreme circumstances, hypothermia and thermal shock can result. Above 44° C., the patient's tissues may be damaged locally. Increase of central body temperature over certain values can also result in serious complications, systemic damages and potentially fatal complications for the patient. In addition, the fluid is likely to evaporate, thereby resulting in a loss of fluid and again a loss of efficiency. There is a tendency to overheat the drug to compensate for the drop in temperature from the treatment area (usually at room temperature) to the patient's cavity to reach the efficient temperature of the drug and to compensate for the loss of fluid due to evaporation.

To warranty homogeneity of fluid and heat distribution in the cavity vigorous manual agitation of the peritoneal content and drug is required. This kind of technique has shown its effectiveness in several clinical publications, but has also shown a number of practical problems and limitations, and side effects as explained above. Due to the complexity and risks of this procedure, clinicians often opt for a less traumatic, but less efficient, adjuvant treatment after cytoreductive surgery.

Other techniques, referred to as "closed" techniques, have been developed in an attempt to reduce the complexity and invasiveness of the open/coliseum technique. The risk of evaporation and loss of heat is minimal since the cavity is not opened and the procedure is less traumatic. However, these techniques were found to be less efficient and the results less reproducible than those obtained with the open techniques. This is probably related to the difficulty of ensuring the homogeneous distribution of the chemotherapeutic drug and temperature inside a closed cavity. As the drug is introduced into the cavity, they will either stagnate or slowly and naturally migrate around the organs within cavity and, in the absence of the manual agitation used in the "open" technique, the drug may not come into contact with all the areas to be treated. This is a significant disadvantage, in particular where post-surgical chemotherapeutic treatment is required, in which the drug must be applied and administered to all target areas and adjacent areas in order to prevent the recurrence of tumoral cells.

It is an object of this invention to mitigate problems such as those described above.

According to a first aspect of the invention, there is provided an apparatus for providing fluid agitation inside a patient's body cavity, said apparatus comprising at least a gas source; means for delivering gas from the gas source into a patient's body cavity; and means for recovering gas from the patient's body cavity; such that substantially all the fluid present in the cavity is agitated.

With the apparatus according to the present invention, the risk of adverse effects such as those encountered in the "open" techniques is reduced. In addition, a homogeneous distribution of fluid and heat throughout the patient's cavity can be achieved to prevent the recurrence of cancerous cells. It is also important to note that the apparatus according to the present invention is versatile in that it can be used in combination with any treatment involving the administration of a fluid in a patient's cavity.

Preferably, the fluid is agitated with a controlled pressure within the patient body cavity. In a preferred embodiment, the apparatus comprises means to monitor the volume of gas delivered to the patient's body cavity and the volume of gas recovered from the patient's body cavity. If the amount of gas delivered to the cavity exceeds the amount of gas recovered from the cavity, then there is a risk of a pocket of gas forming within the patient's body cavity such that the fluid cannot be distributed homogeneously throughout the patient's cavity and in particular to the patient's tissue surrounded such a gas pocket. The present invention minimises or eliminates this risk.

In a preferred embodiment, the apparatus comprises a tubing system comprising at least an inlet tube to deliver gas into the patient's cavity and at least an outlet tube to recover gas from the patient's cavity; and means for circulating gas through the tubing system.

Different gases can be used depending on the applications and treatments, but preferably biocompatible gases, chemically stables and specially with low capillary absorbance rates should be recommended in order not to react with the therapeutic fluid principles and/or to not be incorporated to the patient bloodstream generating potential embolism. The gas source should be according to medical standards. Carbon dioxide is the preferred gas within the context of the present invention because it has a low blood absorbance capacity and therefore the risk of embolism is minimal. In addition, recent publications describe, in animal models, the potential anti-tumoral therapeutic effect of carbon dioxide when delivered at specific pressures in the peritoneal cavity.

The apparatus preferably comprises means for heating or cooling the gas before delivery into the patient's cavity. Preferably, the apparatus comprises means for controlling the temperature of the gas before delivery into the patient's cavity. Also preferably, the apparatus comprises a temperature sensor in the patient s cavity. As explained above, an accurate control of the temperature of any fluid or gas delivered into the patient's cavity is critical in this type of treatment in order to achieve optimum efficiency and minimal risk to the patient. In the case of gas delivery, the temperature of the gas will also be an influencing factor as well as the flow and pressure of the gas delivered into the patient's cavity.

The apparatus preferably comprises means for controlling the gas flow and/or the gas pressure in the tubing system and/or the body cavity. The flow and pressure of the gas delivered to and recovered from the patient's cavity must be adjusted. Too low a pressure will result in an insufficient agitation of the fluid in the cavity, while too high a flow might result in an excess of gas being delivered and potential injury to the patient. The inlet and outlet flow and pressure should be adjusted so that all the gas introduced into the cavity is removed. In addition, if the flow and pressure are not adjusted correctly, excess gas may remain in the patient's cavity causing health complications. The apparatus may additionally comprise a pressure sensor system and/or relieving valves to monitor the pressure in the apparatus and prevent potential over-pressure.

Preferably, the inlet tube comprises an on-line pressure sensor and/or a temperature sensor for measuring the pressure and/or temperature of the gas delivered to the patient's cavity. Also preferably, the outlet tube comprises an on-line pressure sensor and/or a temperature sensor for measuring the pressure and/or temperature of the gas recovered from the patient's cavity. On-line sensors are located within the tube to measure the temperature, flow and/or pressure of the gas. This type of sensor is particularly advantageous in that they facilitate the insertion of the tube into the patient and minimise the risk of injury to the patient, when compared to sensors arranged on the tube or extending from the outer surface of the tube.

Preferably, the inlet tube further comprises means for releasing gas into the patient's cavity in the form of bubbles. The release of the gas in the form of bubbles result in a "Jacuzzi effect" in which the bubbles creates a turbulence and agitate the fluid content of the patient s cavity. This presents the advantages of being minimally disruptive to the patient and of ensuring a homogeneous distribution of the fluid and heat throughout the cavity.

The gas release means may comprise a plurality of apertures in fluid communication with the gas source. The flow of gas circulates through the tubing system and exits into the patient's cavity through the plurality of apertures thereby generating a large number of gas bubbles. The diameter of the aperture will dictate the size of the bubbles generated by the gas release means, which in turn will affect the intensity of the turbulence and hence the agitation of the fluid within the cavity.

The apparatus may further comprise a fluid delivery system. The agitation method of the present invention may be used in combination with any system for the delivery or recirculation of a fluid within a patient's cavity. The apparatus of the present invention may be used in parallel with a fluid delivery or recirculation system or physically combined with such a system. The fluid circulation system as described in the Inventor's own WO 2012/084268 is an example of a preferred system to be used with the agitation system according to the present invention.

The fluid delivery system may comprise means for controlling the temperature of the fluid, means for heating or cooling the fluid and/or one or more sensors for measuring the temperature of the fluid entering the patient's cavity, of the fluid recovered from the patient's cavity and/or in the patient's cavity. The fluid delivery system preferably comprises means for controlling the flow and/or pressure in the fluid and/or one or more sensors for measuring the flow and/or pressure entering the patient's cavity or exiting from the patient's cavity.

The fluid delivery system may be a fluid circulation system in which the fluid is delivered to the patient's cavity and subsequently recovered. The agitation apparatus may comprise a fluid pumping unit for the fluid delivery system working independently or in coordination with the gas pumping unit.

The fluid delivery system may comprise means for selectively removing contaminants from the system. In use, the system may become contaminated with solid contaminants, such as small segments of patient's tissues, which can potentially block the tubing system and/or be sucked into the pumping unit and cause damage. In order to prevent this, solid contaminants may be separated from the fluid, for example by means of a filter or an on-line filter and subsequently removed from the fluid delivery system. The same type of removal means may be used in the agitation apparatus, to separate potential contaminants from the gas and subsequently removed from the gas circulation system.

In a preferred embodiment, the apparatus further comprises a device for separating fluid recovered from the patient's cavity from gas recovered from the patient's cavity. Some fluid will be inevitably mixed with the gas leaving the patient's cavity. The gas-fluid separation device is particularly advantageous when the recovery of the gas and/or the fluid is required. The gas can be recovered for recirculation in the agitation system, while the fluid can be recovered for recirculation in a fluid circulation system.

The separation device may comprise at least a chamber for receiving the fluid and gas recovered from the patient's cavity and the chamber comprises at least an inlet port for recovering fluid and gas from the patient's cavity. The gas-fluid mixture enters the chamber through the inlet port and is received in the chamber in which they can be separated for example by decantation. The heavier fluid will settle at the bottom of the chamber, while the lighter gas will accumulate above the fluid.

The chamber may comprise at least an outlet port for extracting the gas from the chamber and in gas communication with the outlet tube. The gas which has accumulated above the fluid is extracted from the chamber through an outlet port and carried to the outlet tube. The outlet port is therefore preferably located in the top portion of the chamber where the gas will accumulate, above the fluid in the bottom portion of the chamber.

The extracted gas may be re-circulated into the tubing system. Once separated from the fluid, the extracted gas may be re-circulated in the agitation system. This is particularly advantageous in procedures in which a large volume of gas is required. Alternatively, the extracted gas may be discarded. Where very small amounts of gas are required, the extracted gas is sometimes merely released into the atmosphere. However, this is not advisable in view of the potential air pollution of the treatment area.

The chamber may comprise at least an outlet port for extracting the fluid from the chamber. Preferably, the outlet port will be located in the bottom portion of the chamber where the fluid will accumulate. In a preferred embodiment, the chamber comprises a detachable base and the outlet port is integrally moulded to said chamber base so that a robust and sealed connection is produced. This base-port part also has the advantage of being relatively easy and therefore inexpensive to produce. The extracted fluid may be re-circulated into a/the fluid delivery system. Alternatively, the extracted fluid may be discarded.

The chamber may comprise condensation means for facilitating the condensation of the fluid. As explained above, the gas-fluid mixture will separate in the decantation chamber. However, some of the therapeutic fluid, in particular where the fluid has been heated, will be present in a gas form in the chamber.

The condensation means may for example comprise one or more condensation surfaces extending from one or more inner surfaces of the chamber. These condensation surfaces increase the surface area available for the therapeutic fluid in a gas form to condensate back into a fluid form and subsequently settle at the bottom of the chamber. The condensation surfaces may be arranged at an angle of more than 0 degrees and less than 90 degrees relative to the inner surface from which the condensation surface extends. The angled surfaces present the advantage of facilitating the fluid recovered from the condensation process to slide down the sloped surfaces and deposit at the bottom of the chamber.

The separation chamber preferably comprises a securing element for securing the separation device to the patient. In its simplest form, the securing element preferably comprises an anchor within the patient having a portion extending from the anchor, through the patient's tissues and extending beyond the patient's skin surface so that it can be secured to the separating device, thereby securing the separating device to the patient.

The securing element may comprise a pin having a pin base and a hollow pin member extending from the pin base, wherein the outer dimensions of the pin member substantially corresponds with the inner dimensions of an aperture in the base of the chamber. The base acts as an anchor within the patient. The pin member extends from the base, through the patient's tissues and extends beyond the skin surface of the patient. The pin is secured to the base of the chamber, thereby securing the separation device to the patient. In a preferred embodiment, the base is substantially flat so that, in use, it lies along the inner surface of the patient's internal abdomen layer. Preferably, the base is devoid of angles and more preferably circular or oval, in order to avoid injury to the patient's tissues. The pin member extends substantially perpendicularly from the pin base so that, in use, the base can lie flat against the patient's skin internal abdomen layer. Preferably the pin member comprises retention means, such as one or more extending ribs, to secure the pin member to the base of the chamber.

The pin may be a/the inlet port for recovering fluid and gas from the patient's cavity. Thus the pin/inlet port allows the passage of gas and fluid from the patient's cavity into the chamber.

The elongate member may be preferably made of a flexible material. Alternatively, the pin (including the base and the elongate member) is integrally formed and made of a flexible material.

The securing element preferably comprises a plug to secure the pin member to the base of the chamber, wherein the plug has an outer dimension greater than the inner dimension of the pin member. The plug can therefore be inserted in the pin member so that it pushes the pin member against the edges of the aperture in the base of the chamber thereby further securing the pin member to the base of the chamber and creating a stronger seal.

The apparatus may further comprise a cover partially surrounding the securing means. For example, the cover element covers the pin member extending into the chamber and the plug. The base of the chamber may comprise a thread-screw portion corresponding to a thread-screw portion of the cover.

The separating device may comprise means for preventing blockage of the inlet port by the patient's tissues. When the gas-fluid mixture is extracted from the patient's cavity, the patient's tissues will be drawn towards the inlet port and can potentially partially or completely block the passage of the gas-fluid mixture and cause injury. The blockage prevention means preferably comprises a filter, which can be arranged within the patient and adjacent the inlet port to prevent the patient's tissues from getting caught or blocking the inlet port. The blockage prevention means is preferably substantially bowl-shaped. This shaped is advantageous is that it creates a clearing around the inlet port and in addition the patient's tissues can slide over its surface.

According to a second aspect of the invention, there is provided a gas-fluid separation device for use with the agitation apparatus as described above.

According to a third aspect of the invention, there is provided a securing element for use with the agitation apparatus as described above.

According to a fourth aspect of the invention, there is provided a method for agitating a fluid within a patient's cavity comprising the use of the agitation apparatus as described above.

According to a fifth aspect of the invention, there is provided a method for administering a therapeutic fluid into a patient's cavity comprising the step of using of the agitation apparatus as described above.

The methods preferably comprise the steps of (a) delivering a fluid within a patient's cavity and (b) agitating the fluid within the cavity using the apparatus as described above.

The methods preferably comprise the additional steps of (c) recovering a gas-fluid mixture from the patient's cavity and (d) separating any fluid recovered in step (c) using the gas-fluid separation device as described above. The methods may also comprise the additional steps of (e) re-circulating the gas recovered from step (c) into the tubing system of the agitation apparatus. The methods may also comprise the step (f) of re-circulating the fluid recovered from step (d) into a/the fluid circulation system.

According to a sixth aspect of the invention, there is provided a method for securing an agitation apparatus as described above to a patient using the securing element as described above.

According to a seventh aspect of the invention, there is provided a method for the separation of a gas from a fluid using the gas-fluid separation device as described above.

The invention will be further described with reference to the accompanying figures, in which:

FIGS. 7A-7D are schematic representations of a chamber base, a pin, a plug and a cover comprised in a securing element according to the present invention;

FIGS. 11A and 11B are schematic representations of a first chamber and cap for use with a gas-fluid separation device according to the present invention; and FIGS. 12A and 12B are schematic representations of a second chamber and cap for use with a gas-fluid separation device according to the present invention.

Figure 1:
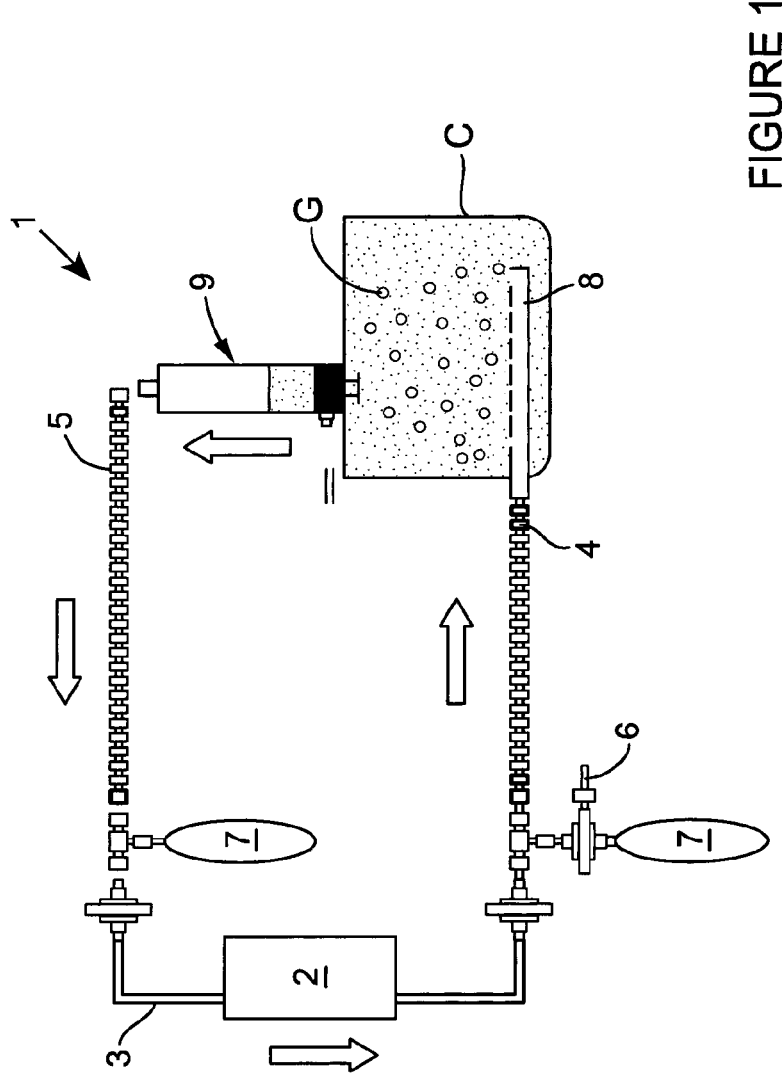
FIG. 1 is a schematic representation of an agitation apparatus according to the present invention.

With reference to FIG. 1, there is illustrated an apparatus 1 for providing fluid agitation inside a patient's body cavity C, said apparatus 1 comprising at least a gas source (not shown); at least a pump 2; at least a tubing system 3, said tubing system 3 comprising at least an inlet tube 4 to deliver gas G into the patient's cavity and at least an outlet tube 5 to recover gas from the patient's cavity.

Gas G, for example carbon dioxide, from the gas source (not shown) is introduced into the tubing system 3 of the agitation apparatus 1 via gas feeding port 6. The tubing system 3 is provided with one or more gas reservoirs, for example gas balloons 7, to increase the gas volume in the agitation apparatus 1. Pump 2 enables the circulation of gas G through the tubing system 3, in the direction as indicated by the arrows in FIG. 1 so that it is released into the patient's cavity through inlet tube 4.

A segment of inlet tube 4 inserted in the patient's cavity C comprises a plurality of apertures 8 through gas G is released in the form of bubbles into the cavity. Any fluid F in the cavity is agitated due to the turbulence caused by the introduction of the gas bubbles and is homogenously distributed and administered to the target area.

The gas exits the patient's cavity through outlet tube 5 to re-enter the tubing system 3. The apparatus shown in FIG. 1 further comprises a gas-fluid separation device 9 intercalated between the patient's cavity and the outlet tube so that any fluid exiting the cavity together with the gas is removed before the gas re-enter the tubing system.

Figure 4:
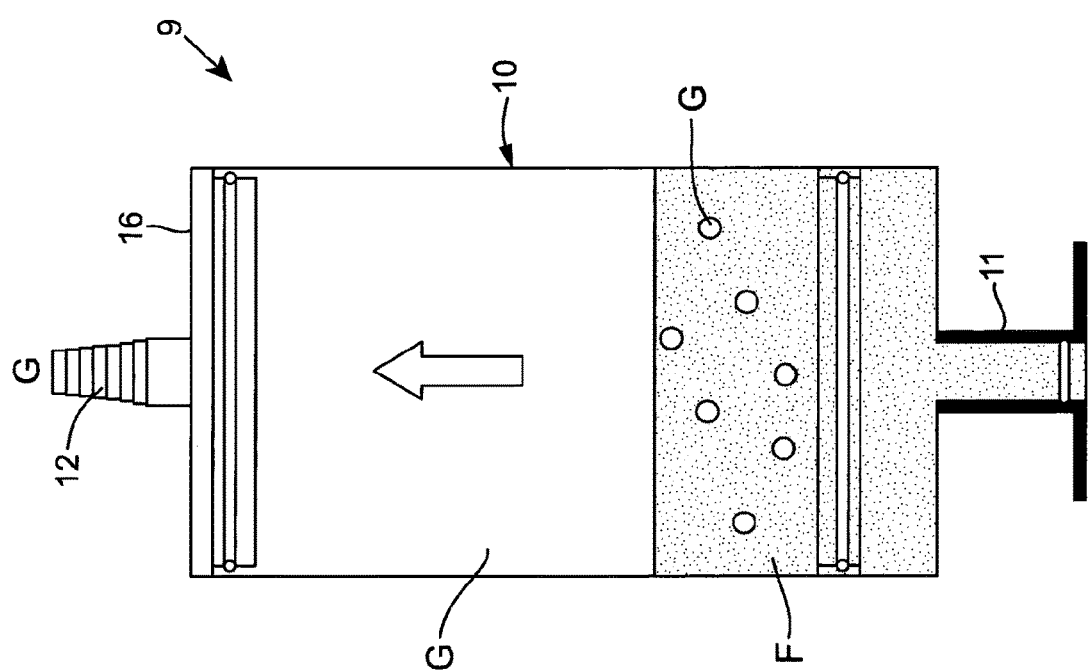
FIG. 4 is a schematic representation of a first gas-fluid separation device according to the present invention.

A device 9 for separating fluid recovered from the patient's cavity from gas recovered from the patient's cavity is shown in FIG. 4. This gas-fluid separation device 9 comprises a chamber 10 for receiving the gas-fluid mixture recovered from the patient's cavity. In this embodiment, the chamber 10 is in the shape of a cylinder.

The chamber 10 comprises a gas inlet port 11 for recovering the gas-fluid mixture from the patient's cavity and a gas outlet port 12 for extracting the gas from the chamber 10. The outlet port 12 is in gas communication with the outlet tube 5 and is located above fluid level in the top portion of the chamber 10. In this embodiment, the outlet port 12 is integrally formed with the chamber cap 16. In the apparatus as shown in FIG. 1, the gas G exiting the gas-fluid separation device 9 is re-circulated into the agitation apparatus 1. The gas G could also be suitably discarded, although this alternative is only advised for small amounts of gas.

Figure 5:
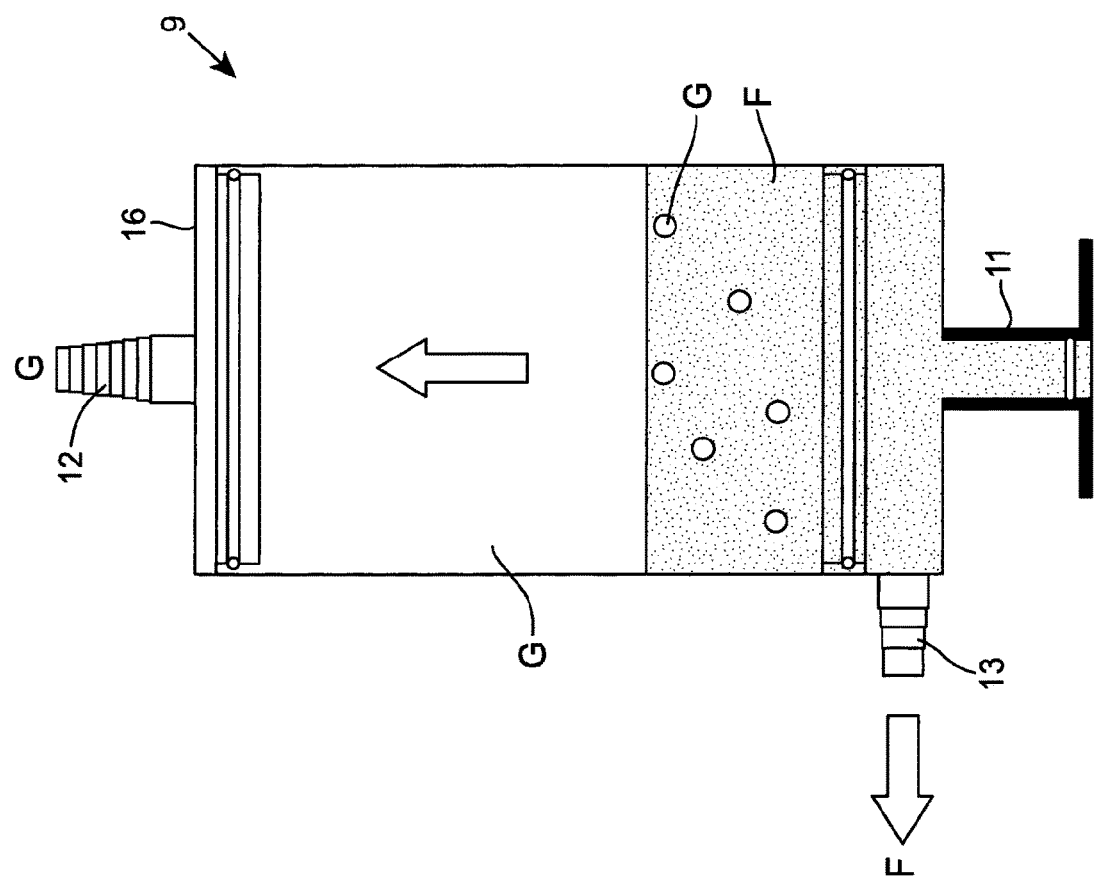
FIG. 5 is a schematic representation of a second gas-fluid separation device according to the present invention.

FIG. 5 shows a second gas-fluid separation device 9 further comprising a fluid outlet port 13 for extracting the fluid F from the chamber 10. The extracted fluid F can be discarded, as shown for example in FIG. 2, or re-introduced into a fluid circulation system 14, as shown in FIG. 3.

Figure 6:
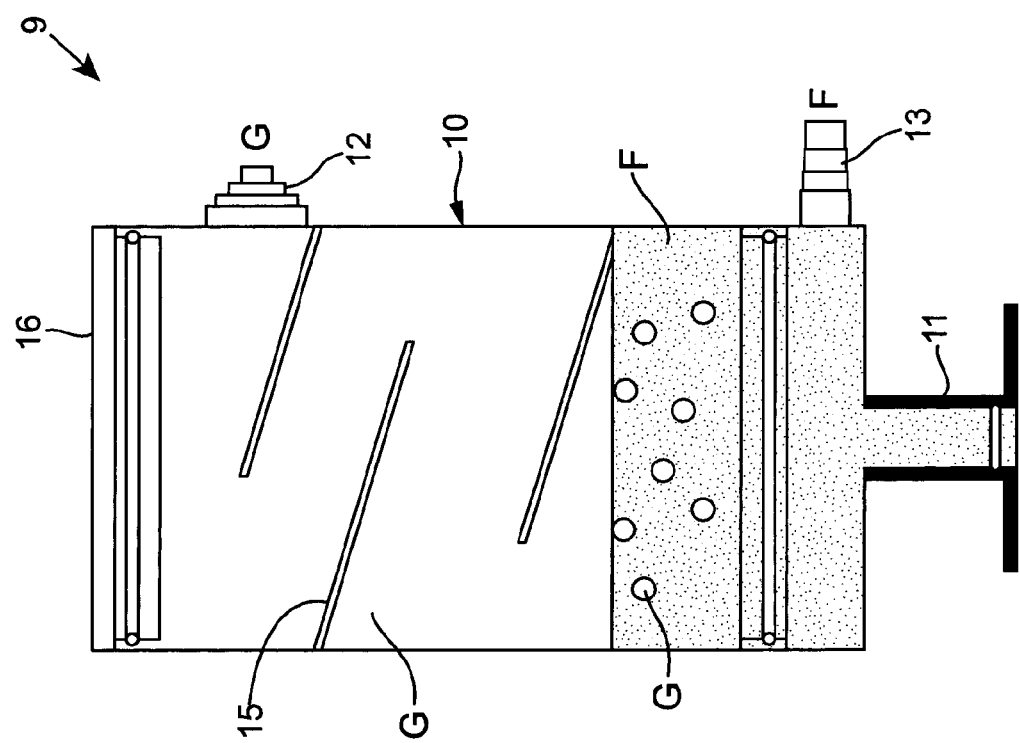
FIG. 6 is a schematic representation of a third gas-fluid separation device according to the present invention.
Figure 8:
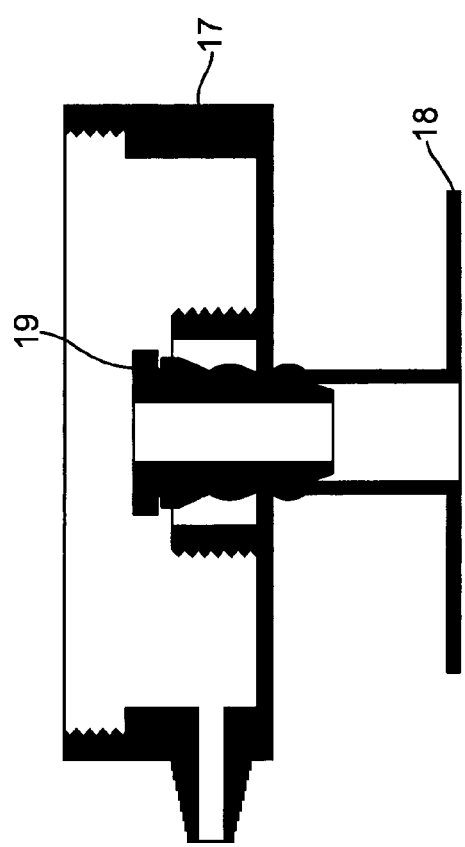
FIG. 8 is a schematic representation of a securing element according to the present invention comprising a chamber base, a pin and a plug.
Figure 9:
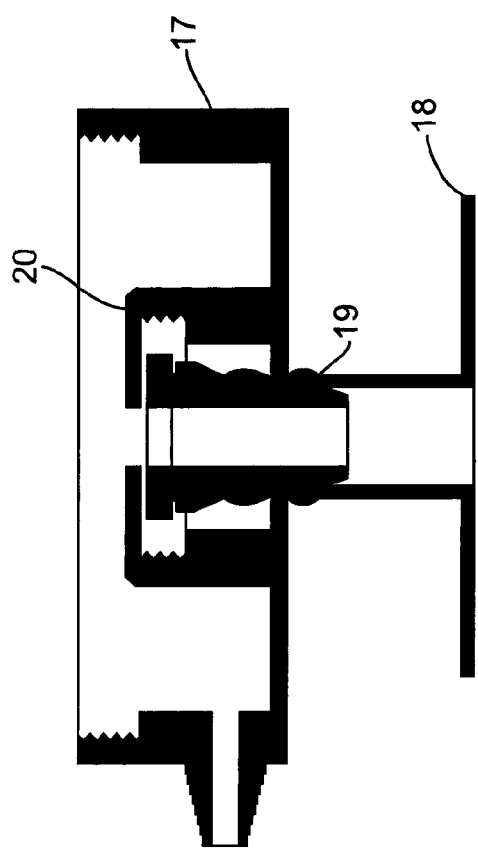
FIG. 9 is a schematic representation of the securing element of FIG. 8 further comprising a cover.

FIG. 6 shows a third gas-fluid separation device 9 in which the gas outlet port 12 is located on a side surface of the chamber 10, but could equally be integrally formed with the cap 16 as shown in FIGS. 4 and 5. In this embodiment, the device 9 comprises means for facilitating the condensation of the fluid F recovered from the patient's cavity. Part of the therapeutic fluid F will be in a gas form, in particular if it has been heated prior to delivery into the patient's cavity, and will mix with the gas G from the agitation apparatus. In the separation device 9 of FIG. 6, the fluid F in a gas form will contact the condensation surfaces 15 and the inner surfaces of the chamber 10 and condensate back into a fluid form, thereby facilitating its separation from gas G.

The condensation means can take any shape which will increase the inner surface area of the chamber 10, however the condensation surfaces 15 shown in FIG. 6 are preferred in that the flat surface prevents the trapping of condensed fluid F, the slope facilitate the movement of the condensed fluid F towards the bottom of the chamber 10, and the design is simple, thereby simplifying the manufacture of the chamber 10. The condensation surface 15 is preferably attached to an inner wall of the chamber 10, may alternatively or additionally be attached to the base of the chamber 10 or to the cap 16 of the chamber 10. The angle between the condensation surface 15 and the surface to which it is attached is more than 0 degree and less than 90 degrees (or more than 90 degrees and less than 180 degrees).

FIGS. 7A to 7D and 8 to 10 depict a chamber base 17, a pin 18, a plug 19, a cover 20 and a filter 21 for use with securing means according to the present invention for securing the separation device to the patient.

In this embodiment, the base 17 of the chamber 10 is detachably connected (e.g. it can be screwed) to the bottom of the chamber 10, and a cap 16 is detachably connected to the top of the chamber 10. Alternatively, the chamber 10, the cap and/or the base 17 can be integrally formed.

The pin 18, in use, is inserted into the patient through an opening and comprises a pin base 18A, and a hollow pin member 18B, in this embodiment a tubular pin extension with an inner channel 18D in fluid/gas communication with the patient's cavity, extending from the pin base 18A. The pin base 18A in this embodiment is a disk which lies flat against the patient's skin [fat layer?], and comprises an aperture 18C in fluid/gas communication with the patient's cavity. In use, the pin member 18B extends through the patient's tissues and exits beyond the opening in the patient's skin. The pin 18 in this embodiment is integrally moulded and made of a flexible plastics material for ease of insertion. Alternatively, the pin member 18B may be made of a flexible plastics material and the pin base 18A may be made of a material different from that of the pin member 18B.

The plug 19 comprises an inner channel 19A in fluid/gas communication with the patient's cavity. The outer dimensions of the plug 19 as such that when inserted into the inner channel 18D of the pin member 18B, the walls of the pin member 18B are pushed against the edges of an opening 17A in the base 17 of the chamber 10 to ensure seal and securing of the pin 18 to the chamber base 17 (see FIG. 8). For additional grip, the plug 19 comprises a ribbed outer surface 19C. For additional seal, the plug 19 comprises a peripheral rim 19B which sits on the end of the pin inner channel 18D.

An optional cover 20 is provided for additional seal and protection of the parts extending into the chamber 10. The cover 20 partially surrounds those parts and comprises an opening 20A in fluid/gas connection with the patient's cavity. The cover 20 in this embodiment is a screw cap with inner screw thread 20B engaging with corresponding screw thread 17B in the base 17 of the chamber 10 (see FIG. 9).

Figure 10:
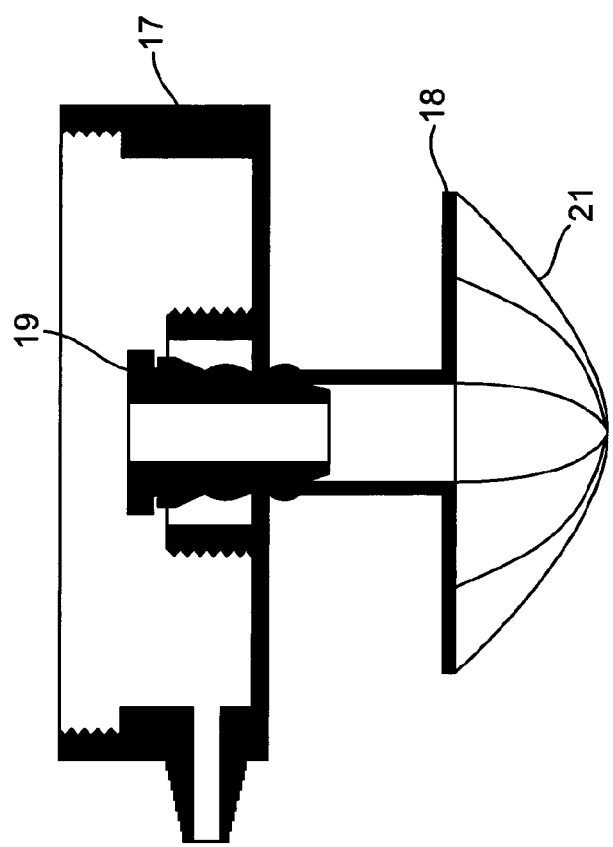
FIG. 10 is a schematic representation of securing element of FIG. 8 further comprising a filter.

With reference to FIG. 10, the separating device 9 comprises means for preventing blockage of the inlet port 11 of the chamber 10 in the form of a bowl-shaped filter 21. The filter 21 is made for example of a mesh which prevents the patient's tissues or other bodies likely to block the passage of the fluid and gas out of the patient. The apparatus 1 can also comprise additional filtration elements (not shown) to retain biologic or chemical elements and avoid contamination of the pumping element, the patient, and/or the environment.

As explained above, the primary function of device 9 is to separate fluid from gas exiting from the patient's cavity. Another important function of the device 9 is to act a visual indicator of the level of fluid in the patient, and therefore of the homogeneity of the distribution of the therapeutic fluid within the patient's cavity. The device 9 is placed on the patient's abdomen, most preferably at the uppermost region of the patient's abdomen. The therapeutic fluid is delivered into the patient's cavity and will fill gradually the cavity from the bottom of the cavity to the top of the cavity. As the fluid level reaches the top of the cavity, it will start rising into the device 9, thereby providing a visual indication that of the level of fluid within the cavity. The practitioner can adjust the delivery of the fluid accordingly in that no fluid in the device 9 will indicate the possible presence of an air pocket within the cavity (where the fluid will not be in contact with the patient's tissue and therefore not administered homogeneously) and the volume of fluid delivered to the cavity can be adjusted. The absence of fluid in the device 9 may also indicate a blockage of the inlet port 11 and the practitioner may unblock the port 11 or reposition the device 9 to prevent hindrance of the port 11 by the patient's tissues. A high level of fluid in the device might indicate an excess of fluid within the cavity, and to enable a uncontaminated separation of the gas from the fluid, the practitioner can adjust the volume of fluid delivered to the cavity.

Coming back to FIG. 1, the inlet tube 4 comprises an on-line temperature sensor (not shown) to monitor the temperature of the gas G entering the cavity C, preferably in a segment of the tube 4 adjacent the point of entry into the patient for an accurate reading. The apparatus 1 also comprises a temperature sensor (not shown) to monitor the temperature inside the patient's cavity. The outlet tube 5 comprises an on-line temperature sensor (not shown) to monitor the temperature of the gas exiting the patient's cavity. The temperature of the gas is adjusted using heating or cooling device (not shown) controlled with a temperature controller (not shown).

Similarly, the inlet tube 4 comprises an on-line flow and/or pressure sensor (not shown) to monitor the flow and/or pressure of the gas entering the cavity and the outlet tube 5 comprises an on-line flow and/or pressure sensor (not shown) to monitor the flow and/or pressure of the gas exiting the cavity. The flow and pressure of the gas is adjusted with a flow/pressure controller (not shown).

The agitation apparatus 1 of the present invention is used with a fluid delivery system (not shown), which only delivers the fluid to the patient's cavity. The fluid delivery system comprises a fluid source and a fluid inlet tube to deliver the fluid into the patient's cavity and optionally, a heating and/or cooling system and corresponding sensor(s) and controller and a pressure and/or flow controlling system. The fluid is extracted and separated using a gas/fluid separation device 9 described above.

Figure 2:
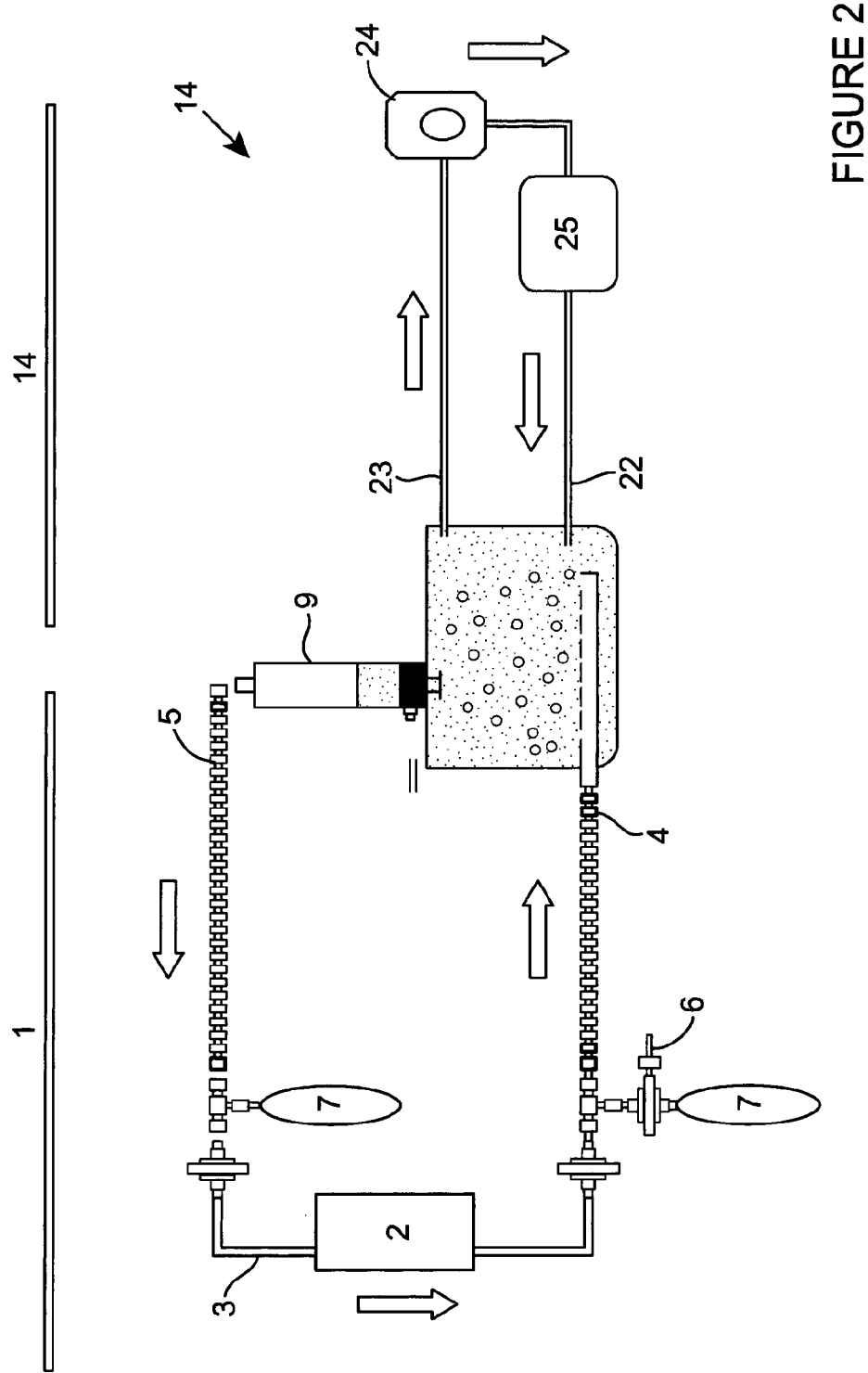
FIG. 2 is a schematic representation of an agitation apparatus according to the present invention used in combination with a fluid circulation system.
Figure 3:
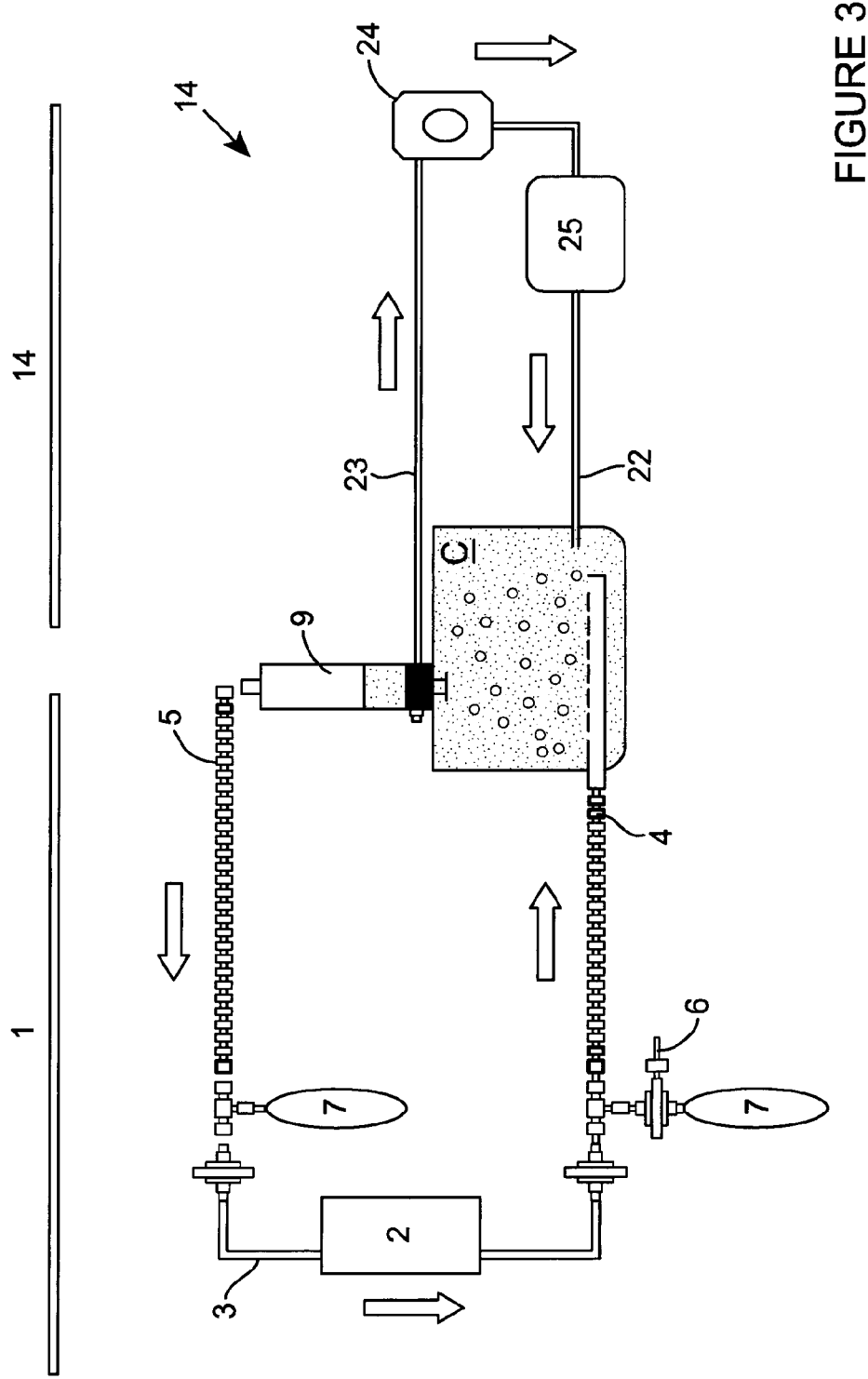
FIG. 3 is a schematic representation of an agitation apparatus according to the present invention comprising a fluid circulation system.

In the set-up shown in FIG. 2, the agitation apparatus 1 of the present invention is used alongside a fluid circulation system 14. The fluid circulation system 14 is a fluid delivery system which also allows the recovery of the fluid from the patient's cavity and the re-circulation of extracted fluid back into the patient's cavity. The fluid circulation system 14 comprises an inlet tube 22 to deliver the fluid into the patient's cavity, an outlet tube 23 to recover fluid from the patient's cavity, a pump 24 (e.g. a peristaltic pump) and a fluid heating/cooling device 25.

In the set-up shown in FIG. 3, the agitation apparatus 1 of the present invention is combined with a fluid circulation system 14. In this embodiment, the outlet tube 23 of the fluid circulation system 14 is connected to the fluid outlet port 13 of the gas/fluid separation device 9 of the agitation apparatus 1 so that the fluid F is recovered from the patient's cavity by the agitation apparatus, separated from the gas G in the gas/fluid separation device 9, and re-circulated through the fluid circulation system 14.

The functioning of present invention will now be described with reference to FIG. 3. In use, the fluid agitation apparatus 1 is connected to the patient as follows. The gas inlet tube 4 is inserted into the patient and positioned adjacent the patient's cavity so that the apertures 8 of the inlet tube 4 are located adjacent the area to be treated.

A small opening is made in the patient adjacent the cavity so that the gas/fluid separation device 9 can be fitted. The pin 18 is inserted in through the opening and positioned so that the pin base 18A lies flat against the patient's tissues and the pin extension 18B extends beyond the opening and the pin aperture 18C and channel 18D are in fluid/gas communication with the patient's cavity. The pin extension 18B engages the aperture 17A of the base 17 of the chamber 10 and further sealed and secured by inserting plug 19A into the channel 18D of the pin extension 18B. The cover 20 is screwed to the screw 17B of the chamber base 17 to partially surround and protect the pin 18 and plug 19.

A therapeutic fluid F is introduced into the patient's cavity C through a fluid circulation system 14 and is circulated by means of a pump 24. The heating/cooling device 25 of the fluid circulation system 14 heats or cools the fluid F. The temperature of the fluid F is adjusted using a temperature controller (not shown) and measured by an on-line temperature sensor (not shown) before entry into the patient. The temperature sensor is arranged within the fluid inlet tube 22 and is located adjacent the point of entry into the patient so that an accurate reading is taken. A further temperature sensor (not shown) is located within the patient's cavity. The flow and pressure of the fluid F is adjusted using a flow and pressure controller (not shown). The pressure of the fluid F is measured by a pressure sensor (not shown) on or in the inlet tube 22.

A gas G, such as carbon dioxide, is introduced into the tubing system 3 of the agitation apparatus 1 through port 6 and is circulated through the apparatus 1 by means of pump 2. The gas G can be heated or cooled and the temperature of the gas G can be adjusted using a temperature controller (not shown). The temperature of the gas G is measured by an on-line temperature sensor (not shown) before entry into the patient. The temperature sensor is arranged within the gas inlet tube 4 and is located adjacent the point of entry into the patient so that an accurate reading is taken. The flow and pressure of the gas G is adjusted using a flow and pressure controller (not shown). The pressure of the gas G is measured by a pressure sensor (not shown) on or in the gas inlet tube 4.

The gas G is released into the patient's cavity C through apertures 8 in the form of bubbles so that turbulence is generated within the cavity C which will agitate the fluid F. The agitation ensures that the fluid F is homogeneously distributed throughout the cavity and administered to the areas to be treated. Thus, the fluid F can reach areas which are hidden in folds or behind organs and tissues which would normally hinder access to those areas.

The gas G and fluid F is recovered from the patient's cavity using a gas/fluid separation device 9 as described above. The bowl-shaped filter 21 as shown in FIG. 10 prevents any tissues or other materials from entering or blocking the inlet port 11 of the separation device 9. The gas-fluid mixture enters the chamber 10 through the inlet port 11. The heavier fluid F deposits at the bottom of the chamber 10, while the lighter gas migrates towards the top of the chamber 10 above fluid level. The condensation of any fluid F in the form of gas is facilitated by the use of condensation surfaces as shown in FIG. 6.

The gas G is removed from the separation chamber 9 through gas outlet port 12 located either at the top or on the side wall of the chamber 10 and above the fluid level. The gas is re-introduced into the tubing system 3 via gas outlet tube 5, which connected to the outlet port 12. The temperature and pressure of the gas G is measured by one or more sensors arranged in or on the gas outlet tube 5. Gas reservoirs or balloons 7 are provided to increase the volume capacity of the agitation system 1 and avoid the use of great lengths of tubing.

The fluid F is removed from the separation chamber 9 through fluid outlet port 13 located at the bottom of the chamber 10, either in the side wall of the chamber 10 or preferably in the base 17 of the chamber 10. The fluid F is re-introduced into the fluid circulation system 14 via fluid outlet tube 23. The temperature, flow and pressure of the fluid F exiting the chamber 10 is measured by one or more sensors arranged in or on the fluid outlet tube 23.

The present invention provides a fluid agitation apparatus and method useful in the delivery and/or recirculation of therapeutic fluids. The apparatus of the present invention can be used for the delivery of heated therapeutic fluids to organs and/or body cavities, like peritoneum, but can also be used for the delivery of therapeutic fluids at different temperatures (cooled or heated) to this or other organs, such as the kidneys, colon, or the liver. The present invention is particularly advantageous in treatments requiring volumes of therapeutic fluid, for example with peritoneum chemo-hyperthermia, in that the agitation warranties the homogeneity of the distribution and of the temperature of the drug throughout the cavity.

The invention claimed is:

1. An apparatus for providing agitation inside a patient's body cavity filled with a therapeutic liquid, said apparatus comprising:
    a gas source;
    at least one inlet tube configured for delivering a gas from the gas source into the patient's body cavity, the at least one inlet tube is configured to be positioned at a first location in the patient's body cavity; and
    a gas-liquid separation device for recovering the gas from the patient's body cavity, the gas-liquid separation device comprising at least one chamber having at least one inlet port for recovering the therapeutic liquid and the gas from the patient's body cavity and at least one outlet port for extracting the gas from the at least one chamber, the at least one inlet port of the gas-liquid separation device configured to be positioned at a second location in the patient's body cavity and the gas-liquid separation device further configured to act as a visual indicator to allow a visual inspection of the level of the therapeutic liquid in the patient's body cavity;
    such that substantially all the therapeutic liquid and peritoneal or fluid content present in the patient's body cavity is agitated.

2. The apparatus of claim 1, wherein the therapeutic liquid is agitated with a controlled pressure within the patient's body cavity.

3. The apparatus according to claim 1, wherein the gas-liquid separation device is configured to monitor the volume of the gas delivered to the patient's body cavity and the volume of the gas recovered from the patient's body cavity.

4. The apparatus according to claim 1, further comprising at least an outlet tube to recover the gas from the patient's body cavity; and a pump for circulating the gas through the at least one inlet tube and the at least one outlet tube.

5. The apparatus according to claim 4, wherein the at least one inlet tube further comprises a plurality of apertures for releasing the gas into the patient's body cavity in the form of bubbles.

6. The apparatus according to claim 5, wherein the plurality of apertures are in fluid communication with the gas source.

7. The apparatus according to claim 4, wherein the gas-liquid separation device is configured for separating the therapeutic liquid recovered from the patient's body cavity from the gas recovered from the patient's body cavity.

8. The apparatus according to claim 7, wherein the at least one chamber comprises a securing element for securing the gas-liquid separation device to the patient, the securing element comprising a pin having a pin base and a hollow pin member extending from the pin base, wherein outer dimensions of the hollow pin member substantially correspond with inner dimensions of an aperture in a base of the at least one chamber.

9. The apparatus according to claim 8, wherein the securing element comprises a plug to secure the pin member to the base of the at least one chamber, wherein the plug has an outer dimension greater than an inner dimension of the hollow pin member.

10. The apparatus according to claim 8, further comprising a cover partially surrounding the securing element.

11. The apparatus according to claim 7, wherein the at least one chamber comprises at least one outlet port in gas communication with the at least one outlet tube for extracting the gas from the at least one chamber.

12. The apparatus according to claim 11, wherein the extracted gas is re-circulated into the at least one inlet tube and at least one outlet tube.

13. The apparatus according to claim 7, wherein the at least one chamber comprises the at least one outlet port for extracting the therapeutic liquid from the at least one chamber.

14. The apparatus according to claim 13, wherein the therapeutic liquid extracted from the at least one chamber is re-circulated into the liquid delivery system.

15. The apparatus according to claim 7, wherein the at least one chamber comprises condensation means for facilitating condensation of the therapeutic liquid, wherein the condensation means comprises one or more condensation surfaces extending from one or more inner surfaces of the at least one chamber.

16. The apparatus according to claim 7, wherein the gas-liquid separation device comprises a filter for preventing blockage of the at least one inlet port by the patient's tissues.

17. The apparatus according to claim 1, including a liquid delivery system for delivering the therapeutic liquid into the patient's body cavity.

18. The apparatus according to claim 17, wherein the liquid delivery system comprises a heating or cooling device for heating or cooling the liquid.

19. The apparatus according to claim 17, wherein the liquid delivery system comprises a flow and pressure controller for controlling the flow and/or pressure of the liquid.

20. The apparatus according to claim 17, wherein the liquid delivery system comprises a filter for selectively removing contaminants from the system.

21. The apparatus according to claim 1, wherein the gas is carbon dioxide.

22. The apparatus according to claim 1, further comprising a heating or cooling device with a temperature controller for heating or cooling the gas before delivery into the patient's body cavity.

23. The apparatus according to claim 1, further comprising a temperature sensor adapted to be in the patient's body cavity.

24. The apparatus according to claim 1, further comprising an on-line flow and/or pressure sensor for controlling a flow and/or a pressure of the gas delivered to and/or recovered from the patient's body cavity.

25. The apparatus according to claim 1, further comprising an on-line pressure sensor and/or a temperature sensor for measuring the pressure and/or temperature of the gas delivered to the patient's body cavity.

26. The apparatus according to claim 1, further comprising an on-line pressure sensor and/or a temperature sensor for measuring the pressure and/or temperature of the gas recovered from the patient's body cavity.

27. The apparatus according to claim 1, further comprising a securing element, wherein the securing element comprises a pin having a pin base and a hollow pin member extending from the pin base, wherein outer dimensions of the hollow pin member substantially correspond with inner dimensions of an aperture in an base of the at least one chamber.

28. The apparatus according to claim 1, wherein the patient's body cavity is in the patient's peritoneal cavity.

29. The apparatus according to 1, wherein the therapeutic liquid is a chemotherapeutic liquid.

30. The apparatus according to claim 1, wherein the at least one chamber is configured to allow the visual inspection of the level of the therapeutic liquid in the patient's body cavity.

31. A method of administering a therapeutic liquid in a patient's body cavity, the method comprising the steps of:
   (a) introducing into a patient's body cavity a therapeutic liquid;
   (b) introducing into the patient's body cavity at least one inlet tube for delivering a gas from a gas source into the patient's body cavity, the at least one inlet tube is configured to be positioned at a first location in the patient's body cavity;
   (c) introducing into the patient's body cavity an inlet port of a gas-liquid separation device comprising at least one chamber for recovering the therapeutic liquid and the gas from the patient's body cavity, the gas-liquid separation device having at least one outlet port for extracting the gas from the at least one chamber, the inlet port of the gas-liquid separation device is configured to be positioned at a second location in the patient's body cavity and the gas-liquid separation device is further configured to act as a visual indicator to allow a visual inspection of the level of the therapeutic liquid in the patient's body cavity;
   (d) delivering the therapeutic liquid within the patient's body cavity; and
   (e) delivering the gas into the patient's body cavity filled with the therapeutic liquid such that substantially all the therapeutic liquid and peritoneal or fluid content within the patient's body cavity is agitated.

32. The method according to claim 31, further comprising the step of:
   (f) recovering a gas-liquid mixture from the patient's body cavity; and
   (g) separating the therapeutic liquid from the gas recovered in step (f) from the patient's body cavity.

33. The method according to claim 32, further comprising the step of:
   (h) re-circulating the gas recovered from step (f) for re-delivery into the patient's body cavity.

34. The method according to claim 33, further comprising the step of:
   (i) re-circulating the therapeutic liquid recovered from step (g) for re-delivery into the patient's body cavity.

35. The method according to claim 31, wherein the patient's body cavity is in the patient's peritoneal cavity.

36. The method according to claim 31, wherein the therapeutic liquid is a chemotherapeutic liquid.

37. A method for securing an agitation apparatus according to claim 1 to a patient comprising securing a securing element of at least one chamber in the gas-liquid separation device of the agitation apparatus to the patient.

38. A method for the separation of a gas from a therapeutic liquid in a gas-liquid mixture in a patient's body cavity, the method comprising the steps of
   delivering the gas from a gas source into the patient's body cavity through at least one inlet tube positioned at a first location in the patient's body cavity such that substantially all the therapeutic liquid and peritoneal or fluid content within the patient's body cavity is agitated;
   recovering the gas-liquid mixture from the patient's body cavity through at least one inlet port positioned at a second location in the patient's body cavity and receiving the recovered gas-liquid mixture in at least one fluid receiving chamber;

decanting the gas-liquid mixture that is received in the at least one fluid receiving chamber to separate the gas from the therapeutic liquid; and extracting the gas from the at least one fluid receiving chamber.

39. The method according to claim 38, wherein the patient's body cavity is in the patient's peritoneal cavity.

* * * * *